(12) United States Patent
Sigmon, Jr. et al.

(10) Patent No.: US 11,839,359 B2
(45) Date of Patent: Dec. 12, 2023

(54) ENDOSCOPE BENDING SECTION

(71) Applicant: Cook Medical Technologies LLC, Bloomington, IN (US)

(72) Inventors: John Crowder Sigmon, Jr., Winston-Salem, NC (US); Shaun D. Gittard, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 94 days.

(21) Appl. No.: 17/341,842

(22) Filed: Jun. 8, 2021

(65) Prior Publication Data

US 2021/0401270 A1    Dec. 30, 2021

Related U.S. Application Data

(60) Provisional application No. 63/044,506, filed on Jun. 26, 2020.

(51) Int. Cl.
*A61B 1/005*   (2006.01)
*A61B 1/00*    (2006.01)
*A61B 1/273*   (2006.01)

(52) U.S. Cl.
CPC .......... *A61B 1/0057* (2013.01); *A61B 1/0055* (2013.01); *A61B 1/00098* (2013.01); *A61B 1/00183* (2013.01); *A61B 1/273* (2013.01)

(58) Field of Classification Search
CPC . A61B 1/00098; A61B 1/0051; A61B 1/0052; A61B 1/0053; A61B 1/0055; A61B 1/0056; A61B 1/0057; A61B 1/0058; A61B 1/008; A61B 1/018; A61B 1/00073; A61B 1/00174; A61B 1/00177; A61B 1/00179; A61B 1/00181; A61B 1/00183
See application file for complete search history.

(56) References Cited

U.S. PATENT DOCUMENTS

| | | | | |
|---|---|---|---|---|
| 3,557,780 | A * | 1/1971 | Sato | A61B 1/0055 600/141 |
| 4,351,323 | A * | 9/1982 | Ouchi | A61B 1/0055 600/149 |
| 4,721,097 | A * | 1/1988 | D'Amelio | A61B 1/00142 600/128 |
| 4,773,395 | A * | 9/1988 | Suzuki | A61B 1/0057 600/149 |
| 4,947,827 | A * | 8/1990 | Opie | A61B 1/00073 600/149 |
| 5,005,558 | A | 4/1991 | Aomori | |
| 5,749,828 | A | 5/1998 | Solomon et al. | |

(Continued)

FOREIGN PATENT DOCUMENTS

GB    2478988    9/2011

OTHER PUBLICATIONS

International Preliminary Report on Patentability in corresponding PCT Application No. PCT/US2021/036340, dated May 31, 2022, 23 pgs.

(Continued)

*Primary Examiner* — Ryan N Henderson
(74) *Attorney, Agent, or Firm* — Crowell & Moring LLP

(57) ABSTRACT

Endoscope systems with bending sections that can bend in four directions independent of the rotatable viewing configuration of the endoscope systems are provided. Methods of using the endoscope systems in a patient's body are further provided.

21 Claims, 11 Drawing Sheets

(56) References Cited

U.S. PATENT DOCUMENTS

| | | | |
|---|---|---|---|
| 5,873,817 A | 2/1999 | Kokish et al. | |
| 6,817,974 B2 | 11/2004 | Cooper et al. | |
| 9,565,994 B2 | 2/2017 | Kappel et al. | |
| 10,029,073 B2 | 7/2018 | Kabe et al. | |
| 10,076,236 B2 | 9/2018 | Ikeda et al. | |
| 10,321,804 B2 | 6/2019 | Jacobsen et al. | |
| 10,363,398 B2 | 7/2019 | Gerrans et al. | |
| 2004/0138529 A1 | 7/2004 | Wiltshire et al. | |
| 2005/0065404 A1* | 3/2005 | Moriyama | A61B 1/018 600/104 |
| 2007/0049800 A1* | 3/2007 | Boulais | A61B 1/0011 600/141 |
| 2007/0244360 A1* | 10/2007 | Ikeda | A61B 1/012 600/116 |
| 2007/0265499 A1* | 11/2007 | Wood | A61B 1/0052 600/137 |
| 2008/0287741 A1 | 11/2008 | Ostrovsky et al. | |
| 2008/0287961 A1* | 11/2008 | Miyamoto | A61B 17/3415 606/127 |
| 2008/0300462 A1 | 12/2008 | Intoccia et al. | |
| 2014/0165772 A1* | 6/2014 | Okazaki | A61B 1/0057 74/490.04 |
| 2015/0359420 A1* | 12/2015 | Hatase | A61B 1/0055 600/110 |
| 2016/0288337 A1 | 10/2016 | Zubiate et al. | |
| 2017/0354318 A1 | 12/2017 | Rogers et al. | |
| 2018/0168432 A1 | 6/2018 | Banik et al. | |
| 2018/0360435 A1* | 12/2018 | Romo | A61B 1/0055 |
| 2019/0038868 A1* | 2/2019 | Elia | A61B 1/0052 |
| 2019/0069764 A1 | 3/2019 | Isoda et al. | |
| 2019/0104923 A1 | 4/2019 | Ostrovsky et al. | |
| 2019/0142413 A1 | 5/2019 | Fairneny | |
| 2019/0328212 A1 | 10/2019 | Nakaji et al. | |

OTHER PUBLICATIONS

International Search Report and Written Opinion in corresponding PCT Application No. PCT/US2021/036340, dated Oct. 8, 2021 (18 pages).

* cited by examiner

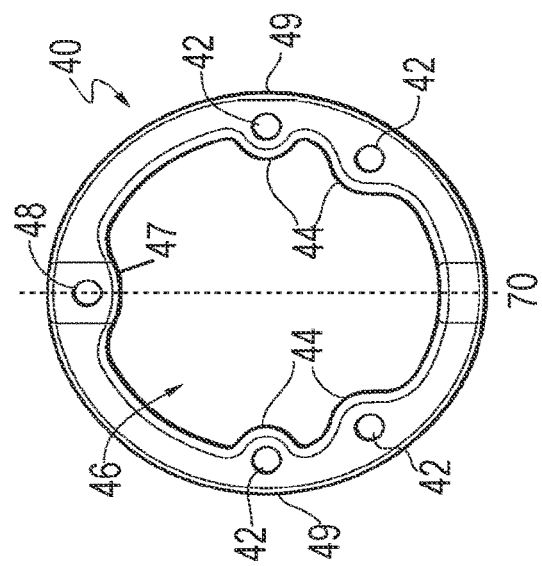
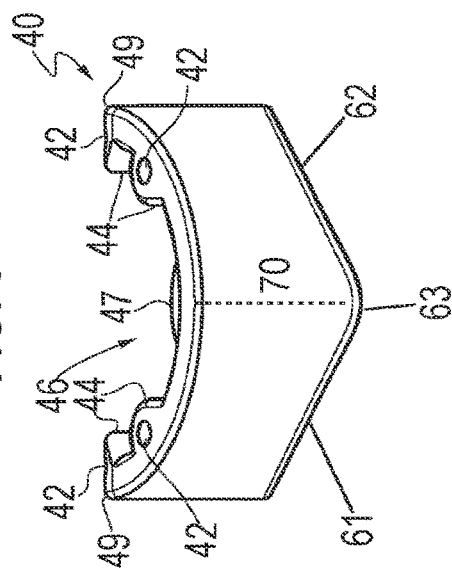
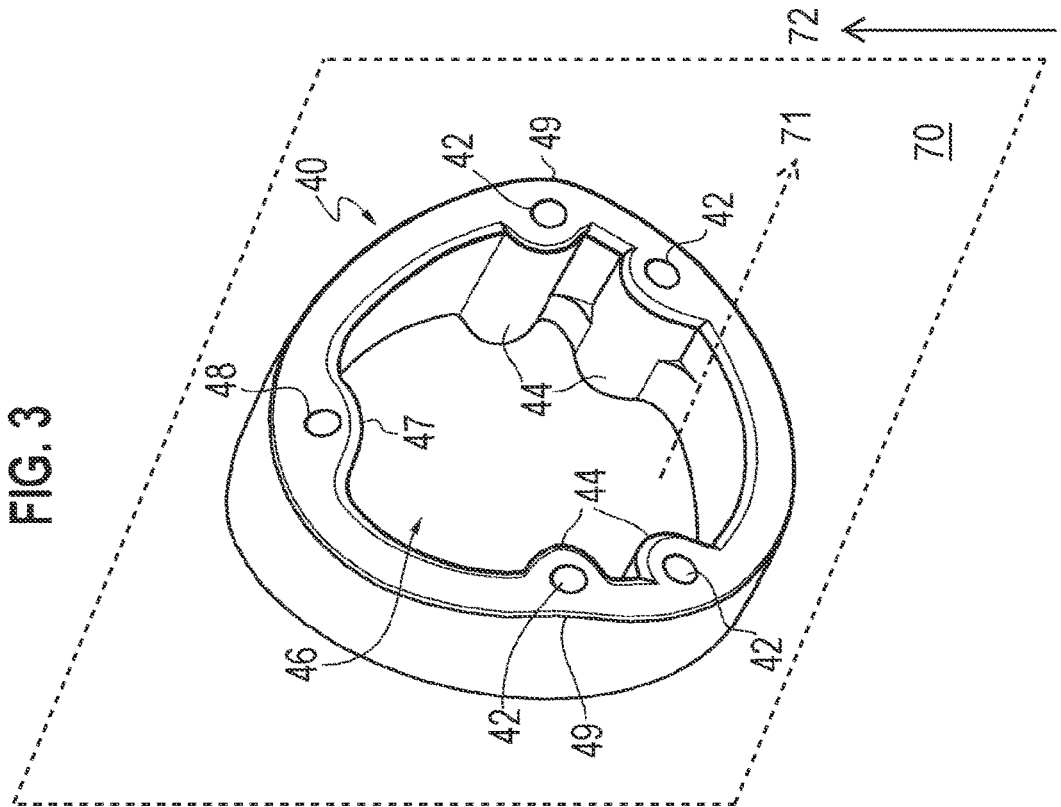

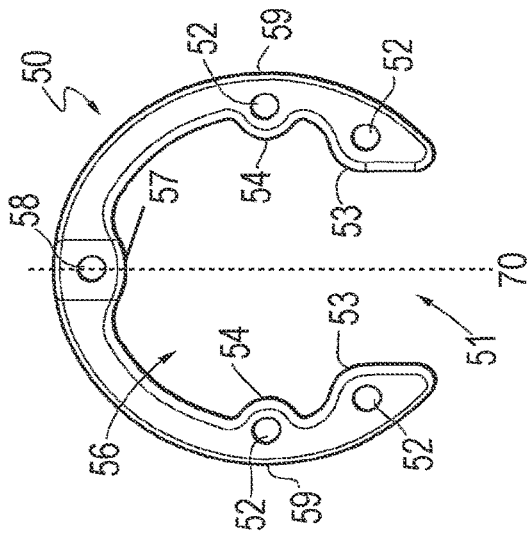
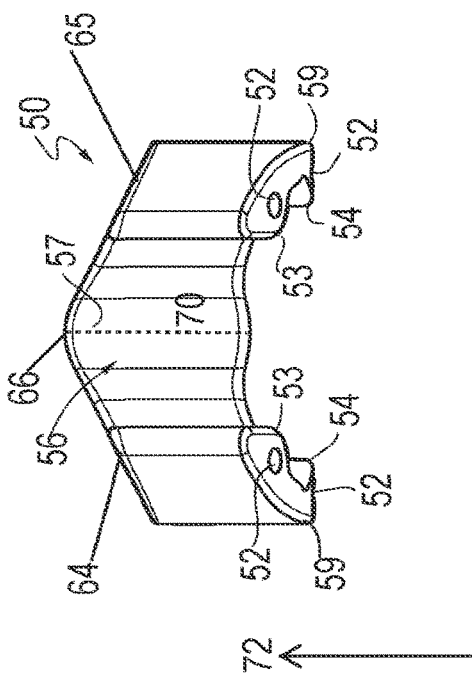
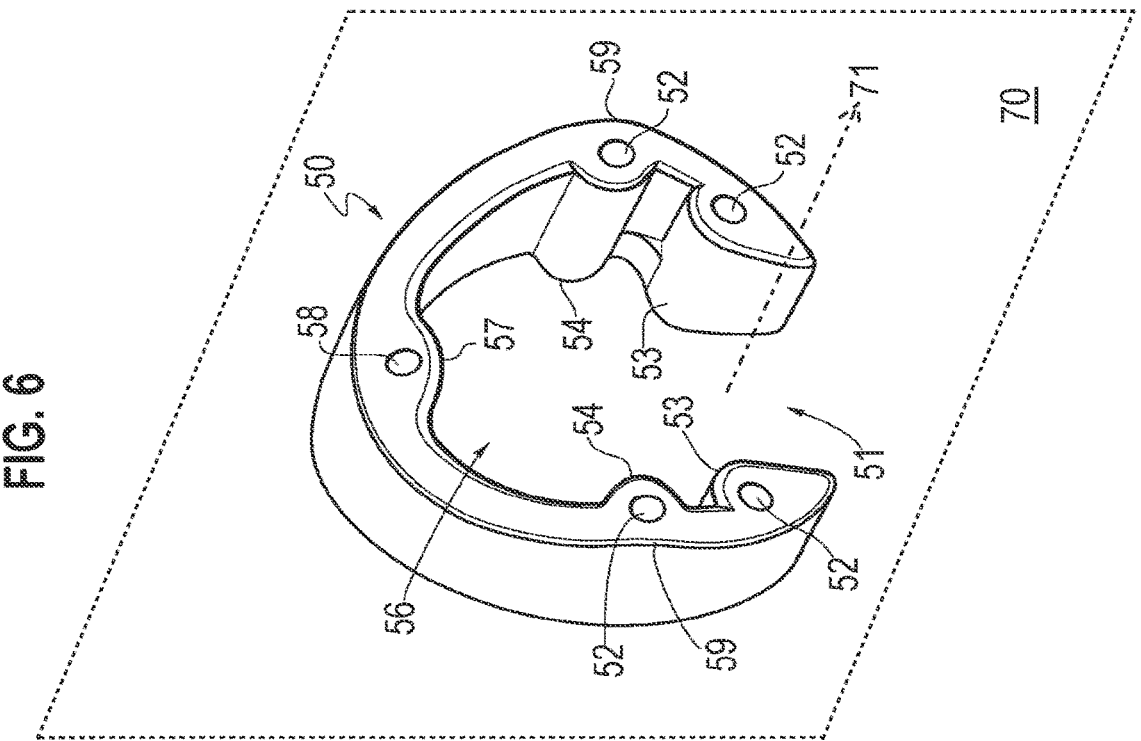

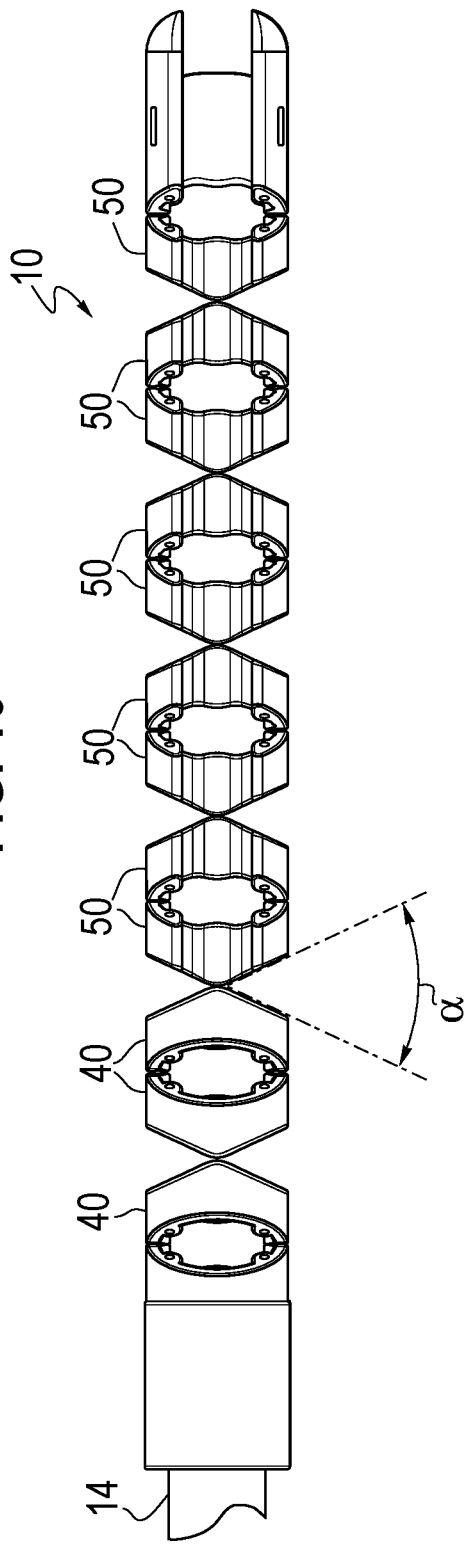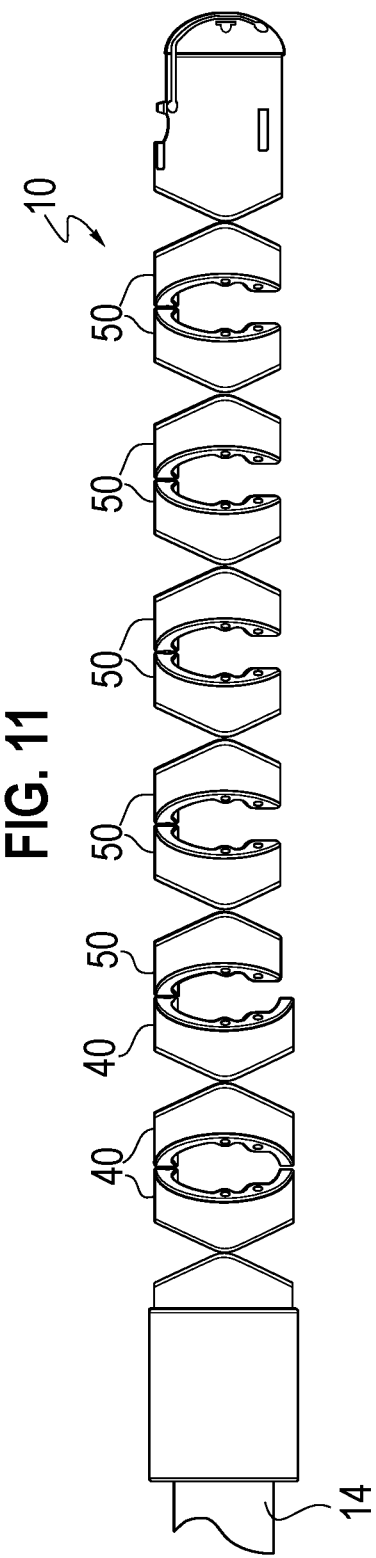

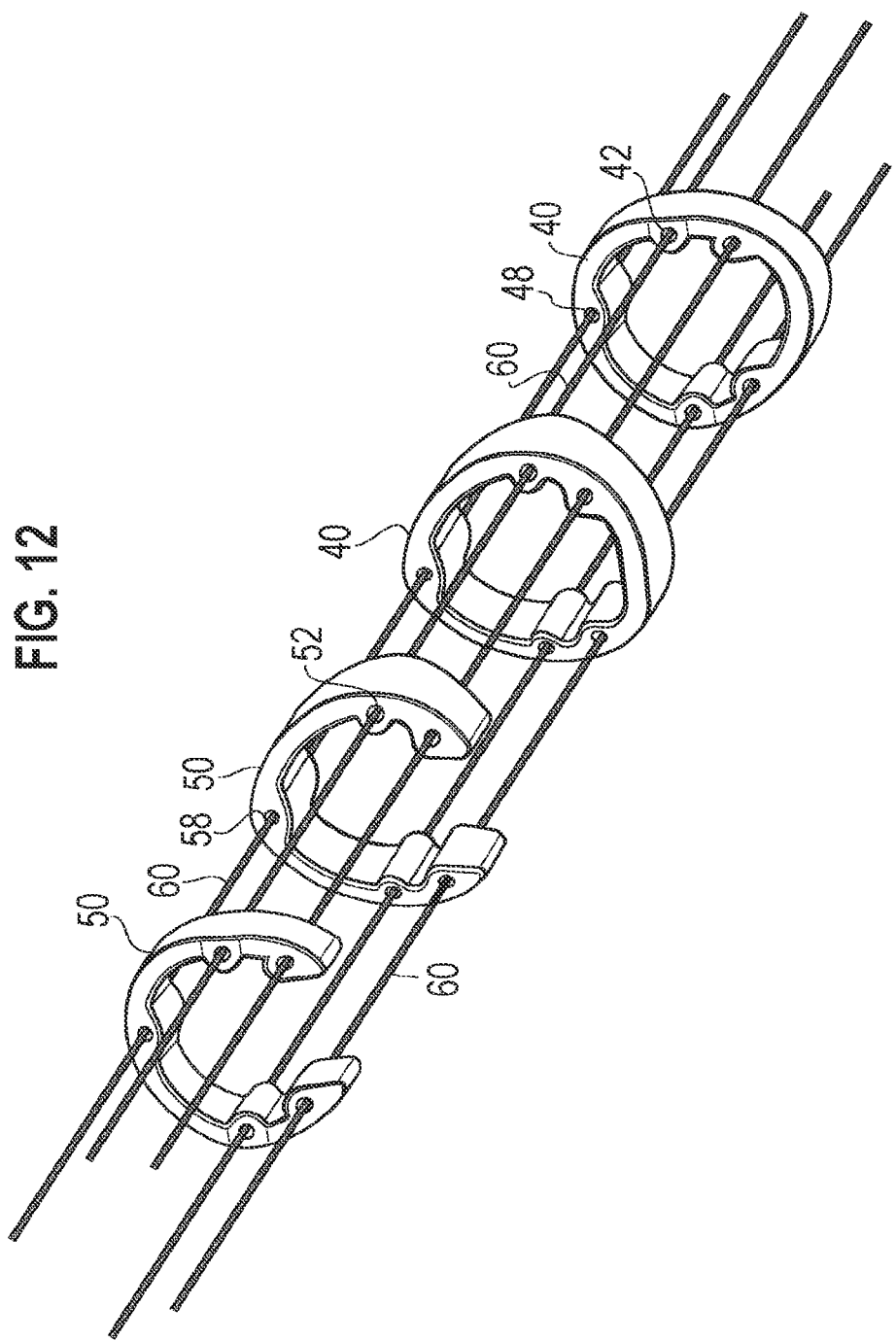

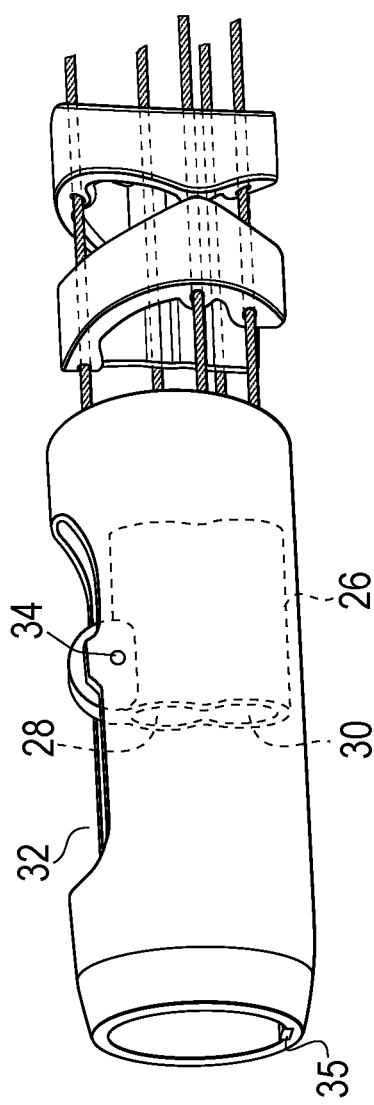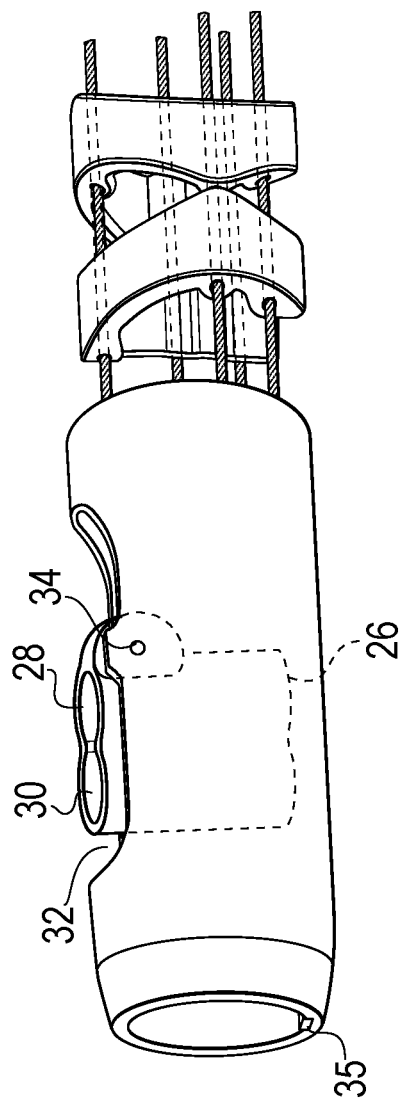

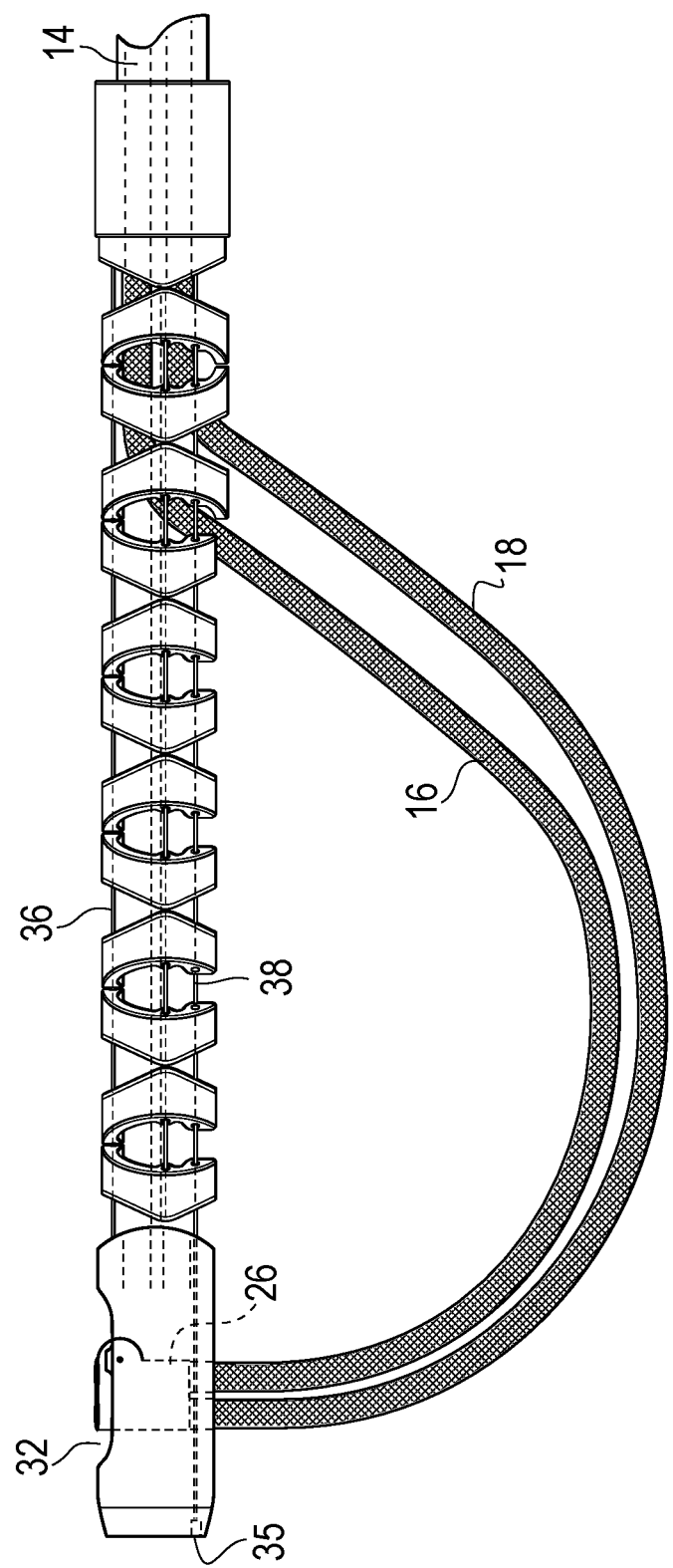

ENDOSCOPE BENDING SECTION

CROSS-REFERENCE TO RELATED APPLICATIONS

This application claims priority from U.S. Provisional Application Ser. No. 63/044,506 filed on Jun. 26, 2020, the entirety of which is hereby incorporated herein by reference.

FIELD

The present disclosure relates to medical devices. More particularly, the present disclosure relates to bending sections for endoscope systems.

BACKGROUND

The statements in this section merely provide background information related to the present disclosure and may not constitute prior art.

The duodenoscope is a medical device used in a variety of endoscopic procedures, including endoscopic retrograde cholangiopancreatography ("ERCP"). In an ERCP, a physician inserts the duodenoscope into a patient's mouth, through the patient's gastrointestinal ("GI") tract, and into the duodenum until the distal end of the duodenoscope is positioned near the papilla of Vater, a small mound-like structure that acts as the entrance from the common bile duct and pancreatic duct into the duodenum. The physician then uses a variety of tools and accessories that are passed through a lumen in the duodenoscope to access the common bile duct or pancreatic duct through the papilla of Vater.

However, the duodenoscope suffers from several design issues. For example, due to the location of the papilla of Vater and shape of the duodenoscope, the endoscope tools or accessories must be bent sharply at (or sometimes more than) 90 degree angles at the distal end of the duodenoscope, which results in significant friction between the tools and duodenoscope and accompanying force transmission loss. Therefore, the accessories must be durable enough to withstand this sharp bend and the physician must apply a greater force to continue to advance the tools than is desired. Further, the built-in camera system of the duodenoscope is side-facing, making it difficult for novices and even experienced physicians to navigate the duodenoscope through the GI tract. Also, traditional duodenoscopes only have one accessory channel, making the use of multiple accessories time intensive and cumbersome. Additionally, duodenoscopes are difficult to clean, which may result in inadequate cleaning of the device after use and potential bacterial contamination of patients during subsequent use of the duodenoscope.

It is desirable to have an endoscope system that eliminates or lessens the force transmission losses of duodenoscopes. Increased and easier maneuverability of an endoscope system through and within the GI tract is desired.

All endoscopes should include a mechanism to bend the distal end so that the physician can steer the endoscope to scan the GI lumen and navigate the GI anatomy. Links of the bending section are intact around the entire circumference of the distal-proximal longitudinal axis of the bending section. However, such bending sections do not allow the accessory channels to bend outwards so that the bending section can advantageously switch between a forward-viewing perspective and a side-viewing perspective. Further, such bending sections may be experimentally inefficient in deflecting with proper degrees of freedom to cannulate a duodenum.

Accordingly, for certain practical applications, 4-way deflection of links with "U"-shaped profiles may be preferable. Thus, there remains a need for further contributions in this area of technology.

SUMMARY

In one form of the present disclosure, a scope system is provided. The scope system includes an elongate tube including a lumen extending therethrough and a distal portion. The scope system further includes at least one accessory channel including a tubular structure including an accessory lumen extending therethrough, the at least one accessory channel movably disposed at least partially within the lumen, the at least one accessory channel including a distal end section. The scope system further includes a first control wire, connected to the distal portion of the elongate tube and extending proximally along the elongate tube. The scope system further includes a second control wire, connected to the distal portion of the elongate tube and extending proximally along the elongate tube, parallel to the first control wire. The scope system further includes a third control wire, connected to the distal portion of the elongate tube and extending proximally along the elongate tube, parallel to the first control wire and the second control wire. The scope system further includes a fourth control wire, connected to the distal portion of the elongate tube and extending proximally along the elongate tube, parallel to the first control wire, the second control wire, and the third control wire. Proximal movement of the first control wire bends the distal portion in a first direction. Proximal movement of the second control wire bends the distal portion in a second direction, the second direction opposite to the first direction. Proximal movement of the third control wire bends the distal portion in a third direction, the third direction perpendicular to the first direction and perpendicular to the second direction. Proximal movement of the fourth control wire bends the distal portion in a fourth direction, the fourth direction opposite to the third direction.

According to another aspect of the present disclosure, a scope system is provided. The scope system includes an elongate tube including a lumen extending therethrough and a distal portion, the distal portion including circumferentially uncontinuous ribs, each of the circumferentially uncontinuous ribs including a rib opening, the rib openings of the circumferentially uncontinuous ribs being coaxial. The scope system further includes a tubular structure including a tubular structure including an accessory lumen extending therethrough, each of the circumferentially uncontinuous ribs surrounding the at least one accessory channel, the at least one accessory channel movably disposed at least partially within the lumen, the at least one accessory channel including a distal end section. The scope system further includes a first control wire, connected to the distal portion of the elongate tube and extending proximally along the elongate tube. The scope system further includes a second control wire, connected to the distal portion of the elongate tube and extending proximally along the elongate tube, parallel to the first control wire. The scope system further includes a third control wire, connected to the distal portion of the elongate tube and extending proximally along the elongate tube, parallel to the first control wire and the second control wire. The scope system further includes a fourth control wire, connected to the distal portion of the elongate tube and extending proximally along the elongate tube, parallel to the first control wire, the second control wire, and the third control wire. Proximal movement of the first control wire bends the distal portion in a first direction. Proximal movement of the second control wire bends the distal portion in a second direction, the second direction opposite to the first direction. Proximal movement of the third control wire bends the distal portion in a third direction, the third direction perpendicular to the first direction and perpendicular to the second direction. Proximal movement of the fourth control wire bends the distal portion in a fourth direction, the fourth direction opposite to the third direction. The at least one accessory channel is reversibly removable from an interior cavity of each of the plurality of circumferentially uncontinuous ribs through the rib openings.

According to yet another aspect of the present disclosure, a method of using a scope system is provided. The method includes the step of inserting an endoscope system into a patient's body, the endoscope system including an elongate tube including a lumen extending therethrough, the elongate tube further including a distal portion; at least one accessory channel including a tubular structure including an accessory lumen extending therethrough, the at least one accessory channel movably disposed at least partially within the lumen, the at least one accessory channel including a distal end section; and parallel control wires, each of the parallel control wires connected to the distal portion of the of the elongate tube and extending proximally along the elongate tube, individual proximal movement of one or more of the parallel control wires bending the distal portion in one of a first direction, a second direction, a third direction, and a fourth direction, the second direction opposite the first direction, the third direction perpendicular to the first direction and perpendicular to the second direction, and the fourth direction opposite the third direction. The method further includes the step of moving one or more of the parallel control wires so as to bend the distal portion in one of the first direction, the second direction, the third direction, and the fourth direction. The method further includes the step of positioning the endoscope system in a forward-viewing configuration, wherein in the forward-viewing configuration the distal end section is substantially parallel to the distal portion. The method further includes the step of moving the endoscope system to a side-viewing configuration wherein in the side-viewing configuration, the distal end section is disposed at an angle of curvature greater than the angle of curvature of the distal portion.

Further areas of applicability will become apparent from the description provided herein. It should be understood that the description and specific examples are intended for purposes of illustration only and are not intended to limit the scope of the present disclosure.

DRAWINGS

In order that the present disclosure may be well understood, there will now be described various forms thereof, given by way of example, reference being made to the accompanying drawings. The components in the figures are not necessarily to scale. Moreover, in the figures, like-referenced numerals designate corresponding parts throughout the different views.

FIGS. 3-5 illustrate views of an example of a circumferentially continuous, ring-shaped rib for an example of an endoscope system constructed according to the principles of the present disclosure;

FIGS. 6-8 illustrate views of an example of a circumferentially continuous, C-shaped, or open rib for an example of an endoscope system constructed according to the principles of the present disclosure;

FIGS. 10 and 11 illustrate detailed views of an example of a distal portion of an endoscope system constructed in accordance with the principles of the present disclosure;

FIG. 12 illustrates another example of ribs of an example of an endoscope system of the present disclosure disposed along a series of control wires;

FIG. 13 illustrates a detailed view of an example of a pivot arm of an example of an endoscope system in a forward-facing configuration;

FIG. 14 illustrates a detailed view of an example of a pivot arm of an example of an endoscope system in a side-facing configuration;

FIG. 15 illustrates a detailed view of a distal portion of an example of an endoscope system in a side-facing configuration;

Figure 1:
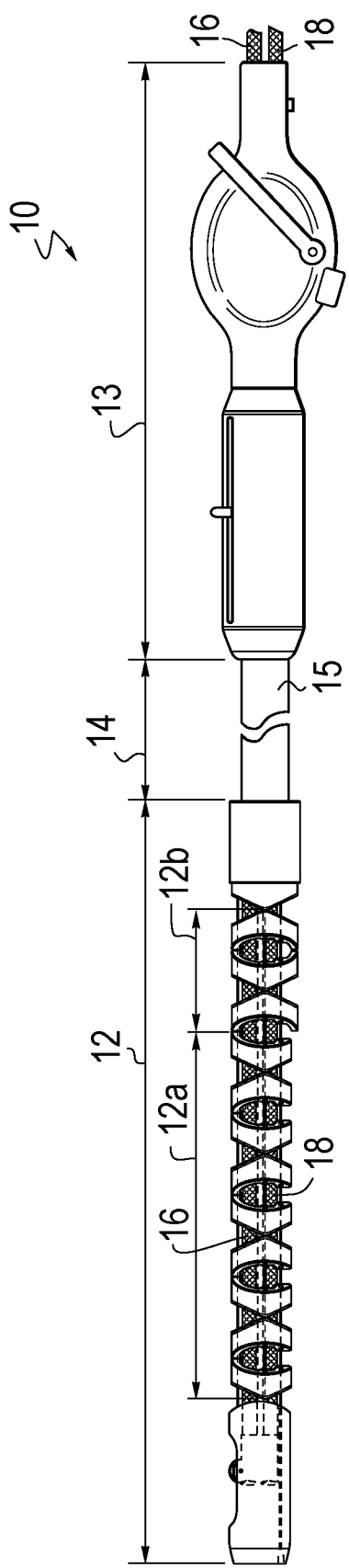
FIG. 1 illustrates a side view of an example of an endoscope system having a bending section according to the principles of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. It should also be understood that various cross-hatching patterns used in the drawings are not intended to limit the specific materials that may be employed in the present disclosure. The cross-hatching patterns are merely exemplary of preferable materials or are used to distinguish between adjacent or mating components illustrated within the drawings for purposes of clarity.

In adding reference denotations to elements of each drawing, although the same elements are displayed on a different drawing, it should be noted that the same elements have the same denotations. In addition, in describing one aspect of the present disclosure, if it is determined that a detailed description of related well-known configurations or functions blurs the gist of one aspect of the present disclosure, it will be omitted.

In the following discussion, the terms "proximal" and "distal" will be used to describe the opposing axial ends of the device, as well as the axial ends of various component features. The term "proximal" is used in its conventional sense to refer to the end of the device (or component) that is closest to the medical professional during use of the assembly. The term "distal" is used in its conventional sense to refer to the end of the device (or component) that is initially inserted into the patient, or that is closest to the patient during use. The term "longitudinal" will be used to refer an axis that aligns with the proximal-distal axis 71 of the device (or component), for example, when the device is not bent. The terms "radially" and "radial" will be used to refer to elements, surfaces, or assemblies relative to one another that may extend perpendicularly from a longitudinal axis. The terms "circumference," "circumferentially," and "circumferential" will be used to elements, surfaces, or assemblies relative to one another encircling or substantially encircling a longitudinal axis at a radius.

The uses of the terms "a" and "an" and "the" and similar references in the context of describing the present disclosure (especially in the context of the following claims) are to be construed to cover both the singular and the plural, unless otherwise indicated herein or clearly contradicted by context. The use of the term "plurality of" is defined by the Applicant in the broadest sense, superseding any other implied definitions or limitations hereinbefore or hereinafter unless expressly asserted by the Applicant to the contrary, to mean a quantity of more than one. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

As used herein, the terms "comprise(s)," "include(s)," "having," "has," "can," "contain(s)," and variants thereof, are intended to be open-ended transitional phrases, terms, or words that do not preclude the possibility of additional acts or structures. The present description also contemplates other examples "comprising," "consisting of," and "consisting essentially of" the elements presented herein, whether explicitly set forth or not.

In describing elements of the present disclosure, the terms $1^{st}$, $2^{nd}$, first, second, A, B, (a), (b), and the like, may be used herein. These terms are only used to distinguish one element from another element, but do not limit the corresponding elements, irrespective of the nature or order of the corresponding elements.

Unless otherwise defined, all terms used herein, including technical or scientific terms, have the same meanings as those generally understood by those skilled in the art to which the present disclosure pertains. Such terms as those defined in a generally used dictionary are to be interpreted as having meanings equal to the contextual meanings in the relevant field of art.

In the context of the present disclosure, a first piece is said to be integral to a second piece if the first and second pieces are formed as a single piece. For example, if the first and second pieces are cast as a single plastic piece, then the first piece is integral to the second piece.

As used herein, the term "about," when used in the context of a numerical value or range set forth, means a variation of ±15%, or less, of the numerical value. For example, a value differing by ±15%, ±14%, ±10%, or ±5%, among others, would satisfy the definition of "about," unless more narrowly defined in particular instances.

Referring to FIG. 1, an example of an endoscope system 10 is illustrated. The endoscope system 10 may be generally shaped as an elongate tube including a distal portion 12, a central portion 14, and a proximal, or handle, portion 13. The central portion 14 may be a flexible, elongate tube with at least one lumen 15 running throughout the length of the central portion 14. The central portion 14 may connect the distal portion 12 and proximal portion 13 together. The at least one lumen 15 of the central portion 14 may extend through the distal portion 12 and handle portion 13 of the endoscope system 10 as well. The central portion 14 may be made of a braided material, such as a polyether block amide (including, for example, PEBAX) with a polytetrafluoroethylene ("PTFE") liner to provide sufficient torquability and pushability. Other potential materials for the central portion 14 include, but are not limited to, polyethylene, polypropylene, and nylon.

The endoscope system 10 may further include two accessory channels 16, 18 each with a lumen running therethrough. The accessory channels 16, 18 may be designed as individual elongated tubes that may be movable within the at least one lumen 15 of the endoscope system 10, thus allowing longitudinal movement of the accessory channels 16, 18 with respect to the central portion 14. While this example includes two accessory channels 16, 18, one or even three or more accessory channels may be included. For example, a single, larger accessory channel may be used to accommodate larger endoscopic tools. Further, in lieu of individual accessory channels 16, 18, a single elongate tube may be used with two or more lumens running through it. The accessory channels 16, 18 may range in diameter anywhere from 1 to 10 millimeters. In one example, accessory channel 16 may be 4.2 millimeters in diameter while accessory channel 18 may be 3.7 millimeters in diameter. The accessory channels 16, 18 may extend proximally from or past the handle portion 13, through the at least one lumen 15 and into the distal portion 12. Various tools, devices, and cameras may be at least partially inserted into and removably disposed in the accessory channels 16, 18.

Figure 2:
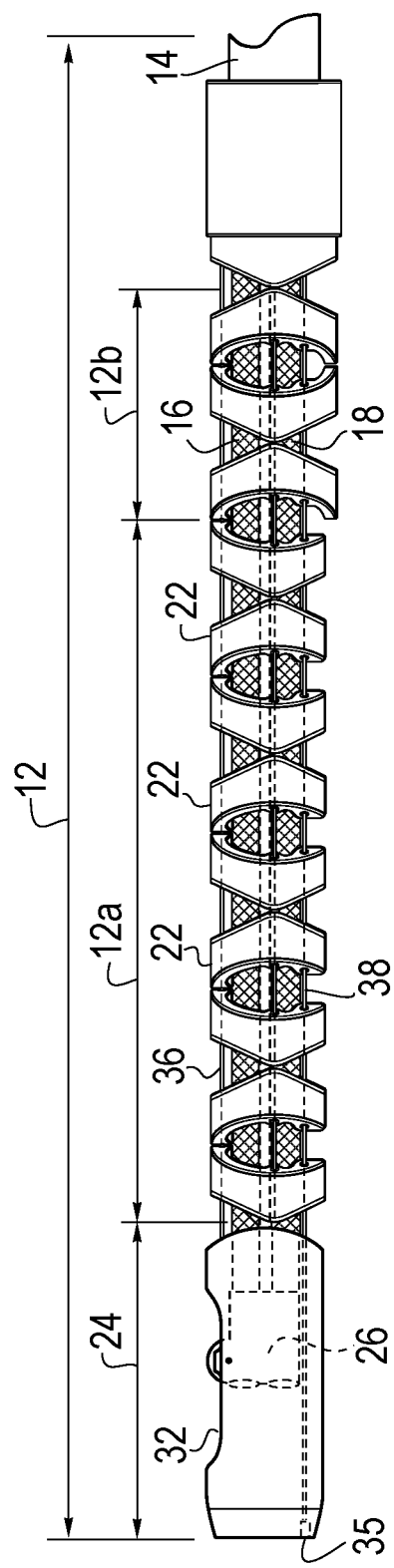
FIG. 2 illustrates a detailed view of a distal portion of an example of an endoscope system in a forward-facing configuration.

Now referring to FIG. 2, a detailed view of the distal portion 12 of an example of endoscope system 10 is illustrated. The endoscope system 10 may include an axially rotatable bearing 80 disposed between the central portion 14 and the distal portion 12, which may allow or permit the distal portion 12 to rotate independently of the central portion 14. The distal portion 12 may have a flexible rib-like construction with multiple individual ribs 22 connected together to create an elongate tube with at least one lumen 15. Ribs 22 may be made of a variety of materials, such as polycarbonate, nylon, polyethylene, polypropylene, and polyoxymethylene. The accessory channels 16, 18 may travel through the ribs 22 to the distal end section 24 of the distal portion 12. The distal end section 24 may include a pivot arm 26 with first and second accessory lumens 28, 30 (shown in FIGS. 13 and 14). The distal ends of the accessory channels 16, 18 may be fixedly or movably disposed within respective first and second accessory lumens 28, 30. The distal end section 24 may also include a side port 32 that provides access from the at least one lumen 15 to a point external the endoscope system 10.

An example of a distal end section 24 of a distal portion 12 is illustrated in more detail in FIGS. 13 and 14. For clarity, the accessory channels 16, 18 are omitted from FIGS. 13 and 14. The pivot arm 26 may be connected or coupled to the distal end section 24 via a pin 34. The pin 34 may create a pivot point, around which the pivot arm 26 may rotate or rotatably pivot with respect to the distal end section 24 to the position shown in FIG. 14. The pivot arm 26 may be moved between a forward-viewing position as shown in FIG. 13 and a side-viewing position as shown in FIG. 14. A light emitting diode ("LED") light 35 may be placed on the distal end section 24 to assist in navigation through a patient's GI tract. Alternatively, the LED light 35 may be placed at other locations on the distal end section 24, such as near the side port 32. Also, multiple LED lights 35 may be used at various locations on the endoscope system 10.

As illustrated in FIGS. 2 and 15, the distal ends of the accessory channels 16, 18 may be secured to the pivot arm 26. Therefore, the accessory channels 16, 18 may rotate with the pivot arm 26 when moving the pivot arm 26 between the side-viewing and forward-viewing configurations. FIG. 2 shows the accessory channels 16, 18 in the forward-viewing configuration, while FIG. 15 shows the accessory channels 16, 18 in the side-viewing configuration. As can be seen in FIG. 15, when in the side-viewing configuration and due to the rotation of the pivot arm 26, distal portions of the accessory channels 16, 18 are bent outside of the confines of the ribs 22 and then curve back towards and into the pivot arm 26. Thus, in the forward-viewing configuration, the angle of curvature or bending radius of the distal portion 12, or angle of distal portion curvature, is the same as the angle of curvature of the accessory channels 16, 18 such that the accessory channels 16, 18 and the distal portion 12 of the endoscope system 10 are substantially parallel; but in the side-viewing configuration, the angle of curvature or bending radius of the accessory channels 16, 18 is greater than the angle of curvature of the distal portion 12 such that distal portions of the accessory channels 16, 18 extend outside the at least one lumen 15 of the distal portion 12.

To move the pivot arm 26 from the forward-viewing configuration to the side-viewing configuration, the accessory channels 16, 18 may be pushed in a distal direction relative to proximal portion 13 and central portion 14, which applies a force through the accessory channels 16, 18 to the pivot arm 26. The resulting force causes the pivot arm 26 to rotate about the pivot point of the pin 34, thereby moving the accessory channels 16, 18 and pivot arm 26 into the side-viewing configuration. To move back to the forward-viewing configuration, a proximal force may be applied to the accessory channels 16, 18 relative to proximal portion 13 and central portion 14, thereby transferring the proximal force to the pivot arm 26. The proximal force then causes the pivot arm 26 to again rotate around the pivot point of the pin 34 in the opposite direction, thereby moving the accessory channels 16, 18 and the pivot arm 26 back to the forward-viewing configuration. To ensure that the accessory channels 16, 18 move in unison during these movements, the accessory channels 16, 18 may be secured together at any point along the length of the endoscope system 10, or even along the entire length. In one example, the accessory channels 16, 18 may be secured together using plastic tubing throughout the entire length of the central portion. In another example, the accessory channels 16, 18 may be secured together at the portions of the accessory channels 16, 18 that extend outside the constraints of the distal portion 12 when the endoscope system 10 is in the side-viewing configuration.

While a pivot arm 26 may be used to assist in transferring the accessory channels 16, 18 between forward-viewing and side-viewing configurations, a variety of other methods and structures may be used. Further, rather than using a pivot arm 26, multiple pivot arms may be used, or one pivot arm may be used for each accessory channel 16, 18. Therefore, each accessory channel 16, 18 may be moved between the forward-viewing and side-viewing configurations independently of each other. Further, the degree of rotation of the pivot arm 26 between the forward-viewing and side-viewing configuration may vary, potential ranging from 45 degrees to greater than 135 degrees.

FIGS. 3-5 illustrate views of an example of a rib 22 for an example of an endoscope system 10 constructed according to the principles of the present disclosure, specifically a ring-shaped rib 40. Each ring-shaped rib 40 may be shaped to allow for minimal contact between the individual ring-shaped ribs 40. Endoscope system 10 may include one or more ring-shaped ribs 40 at the proximal end of the distal portion 12.

FIG. 3 illustrates a perspective view of an example of a circumferentially continuous, or "ring-shaped," rib 40. Ring-shaped rib 40 may be symmetrical about a vertical plane 70 including both the longitudinal axis 71 and vertical axis 72 of endoscope system 10. Vertical axis 72 is perpendicular to longitudinal axis 71. Ring-shaped rib 40 may include an interior cavity 46 in which accessory channels 16, 18 may be disposed such that ring-shaped rib 40 encircles accessory channels 16, 18. Ring-shaped rib 40 may include one or more tab mounts integral to the ring-shaped rib 40 projecting toward the interior cavity 46 of the ring-shaped rib 40. The one or more tab mounts may extend the proximal-distal width of the ring-shaped rib 40. The one or more tab mounts may include a top tab mount 47. The one or more tab mounts may include a proximal-distal top tab mount lumen 48 therethrough. Top tab mount 47 may include top tab mount lumen 48 extending from the proximal end of the top tab mount 47 through to the distal end of the top tab mount 47. The one or more tab mounts may further include one or more side tab mounts 44 projecting toward the interior cavity 46 of the ring-shaped rib 40 from each side of the ring-shaped rib 40. In some examples of a ring-shaped rib 40, the one or more side tab mounts 44 are symmetrically positioned about the vertical plane 70. Each of the one or more side tab mounts 44 includes a proximal-distal side tab mount lumen 42 therethrough. In further examples of a ring-shaped rib 40, each side of the ring-shaped rib 40 may have one side tab mount 44. The ring-shaped rib 40 may include rib side surface points 49 that protrude longitudinally further than the rib top and rib bottom surfaces.

FIG. 4 illustrates a longitudinal proximal-distal cross-sectional view of an example of a ring-shaped rib 40 highlighting the symmetry of the sides of ring-shaped rib 40 about the vertical plane 70 including the longitudinal axis 71, top tab mount 47, and top tab mount lumen 48.

FIG. 5 illustrates a bottom view of an example of a ring-shaped rib 40 highlighting the symmetry of the sides of ring-shaped rib 40 about the vertical plane 70 including the longitudinal axis 71, top tab mount 47, and top tab mount lumen 48 (not shown in FIG. 5). FIG. 5 illustrates the asymmetry of the longitudinal surfaces of ring-shaped rib 40, one longitudinal surface of which will be the proximal surface, and one longitudinal surface of which will be the distal surface. Because ring-shaped ribs 40 will alternate in orientation longitudinally along a distal portion 12 of an endoscope system 10, the distal surface of one ring-shaped rib 40 will correspond to the proximal surface of the next ring-shaped rib 40. Such proximal surface of the next ring-shaped rib 40 will correspond to the distal surface of the subsequent sequential ring-shaped rib 40, and so forth. In a particular ring-shaped rib 40, rib side surface points 49 may be on one longitudinal surface, whether such one longitudinal surface faces the proximal end or the distal end of the endoscope system 10, and planar side longitudinal surfaces 61, 62 may be on the opposite longitudinal surface. Planar side longitudinal surfaces 61, 62 may intersect at intersection surface 63. Planar side longitudinal surface 61 may be co-planar to a plane that is at an acute angle (i.e., less than 90 degrees) relative to a plane that perpendicularly cross-sects the proximal-distal longitudinal axis 71, perpendicular to vertical plane 70. Planar side longitudinal surface 62 may be co-planar to a second plane that is at an acute angle relative to the plane that perpendicularly cross-sects the proximal-distal longitudinal axis 71. A ring-shaped rib 40 may generally have a 90 degree rotation-reflection symmetry about an axis parallel to, or the same as, the longitudinal axis 71, alternatively referred to by those of ordinary skill as an improper axis of rotation, and more particularly, an $S_4$ symmetry axis. In other words, each ring-shaped rib 40 may be generally symmetrical when rotated 90 degrees about the longitudinal axis, and reflected through the longitudinal axis 71, such that rib side surface points 49 may also be intersection surfaces of two planar longitudinal surfaces, each of which may be co-planar to a plane that is at an acute angle relative to the plane that perpendicularly cross-sects the proximal-distal longitudinal axis 71. Such rotation-reflection symmetry may be without respect to the positions of any tab mounts or tab mount holes, which may not be included in the rotation-reflection symmetry.

FIGS. 6-8 illustrate views of another example of a rib 22 for an example of an endoscope system 10 constructed according to the principles of the present disclosure, specifically a circumferentially uncontinuous rib 50, which may be generally "C-shaped" in some examples. Each circumferentially uncontinuous rib 50 may be shaped to allow for minimal contact between the individual circumferentially uncontinuous ribs 50. Endoscope system 10 may include one or more circumferentially uncontinuous ribs 50 in the distal portion 12 between the distal-most ring-shaped rib 40 and the distal end section 24.

FIG. 6 illustrates a perspective view of an example of a circumferentially uncontinuous rib 50. Circumferentially uncontinuous rib 50 may be symmetrical about a vertical plane 70 including the longitudinal axis 71 of endoscope system 10. Circumferentially uncontinuous rib 50 may include an interior cavity 56 in which accessory channels 16, 18 may be disposed such that circumferentially uncontinuous rib 50 generally surrounds accessory channels 16, 18 and accessory channels 16, 18 may be reversibly removed from interior cavity 56 by passing accessory channels 16, 18 through bottom rib opening 51. Bottom rib opening 51 interrupts the circumferential continuity of circumferentially uncontinuous rib 50. Circumferentially uncontinuous rib 50 may include one or more tab mounts integral to the circumferentially uncontinuous rib 50 projecting toward the interior cavity 56 of the circumferentially uncontinuous rib 50. The one or more tab mounts may extend the proximal-distal width of the circumferentially uncontinuous rib 50. The one or more tab mounts may include a top tab mount 57. The top tab mount 57 may include a proximal-distal top tab mount lumen 58 therethrough. Top tab mount lumen 58 extends from the proximal end of the top tab mount 57 through to the distal end of the top tab mount 57. The one or more tab mounts may further include rib opening-adjacent tab mounts 53, which may be flush with surfaces of the circumferentially uncontinuous rib 50 defining bottom rib opening 51. In some examples of a circumferentially uncontinuous rib 50, the rib opening-adjacent tab mounts 53 are symmetrically positioned about the vertical plane 70. Each of the rib opening-adjacent tab mounts 53 includes a proximal-distal side tab mount lumen 52 therethrough. In some examples of a circumferentially uncontinuous rib 50, the circumferentially uncontinuous rib 50 may further include one or more side tab mounts 54 positioned between each rib opening-adjacent tab mount 53 and the top tab mount 57. Each of the one or more side tab mounts 54 includes a proximal-distal side tab mount lumen 52 therethrough. The circumferentially uncontinuous rib 50 may include rib side surface points 59 that protrude longitudinally further than the rib top surface.

FIG. 7 illustrates a longitudinal proximal-distal cross-sectional view of an example of a circumferentially uncontinuous rib 50 highlighting the symmetry of the sides of circumferentially uncontinuous rib 50 about the vertical plane 70 including the longitudinal axis 71, top tab mount 57, and top tab mount lumen 58.

FIG. 8 illustrates a bottom view of an example of a circumferentially uncontinuous rib 50 highlighting the symmetry of the sides of circumferentially uncontinuous rib 50 about the vertical plane 70 including the longitudinal axis 71, top tab mount 57, and top tab mount lumen 58 (not shown in FIG. 8). FIG. 8 illustrates the asymmetry of the longitudinal surfaces of circumferentially uncontinuous rib 50, one longitudinal surface of which will be the proximal surface, and one longitudinal surface of which will be the distal surface. Because circumferentially uncontinuous ribs 50 will alternate in orientation longitudinally along a distal portion 12 of an endoscope system 10, the distal surface of one circumferentially uncontinuous rib 50 will correspond to the proximal surface of the next circumferentially uncontinuous rib 50. Such proximal surface of the next circumferentially uncontinuous rib 50 will correspond to the distal surface of the subsequent sequential circumferentially uncontinuous rib 50, and so forth. In a particular circumferentially uncontinuous rib 50, rib side surface points 59 may be on one longitudinal surface, whether such one longitudinal surface faces the proximal end or the distal end of the endoscope system 10, and planar side longitudinal surfaces 64, 65 may be on the opposite longitudinal surface. Planar side longitudinal surfaces 64, 65 may intersect at intersection surface 66. Planar side longitudinal surface 64 may be co-planar to a plane that is at an acute angle relative to a cross-sectional plane that perpendicularly cross-sects the proximal-distal longitudinal axis 71. Planar side longitudinal surface 65 may be co-planar to a second plane that is at an acute angle relative to the plane that perpendicularly cross-sects the proximal-distal longitudinal axis 71. A circumferentially uncontinuous rib 50 may generally have a 90 degree rotation-reflection symmetry about an axis parallel to, or the same as, the longitudinal axis 71, alternatively referred to as an improper axis of rotation, and more particularly, an $S_4$ symmetry axis. In other words, each circumferentially uncontinuous rib 50 may be generally symmetrical when rotated 90 degrees about the longitudinal axis 71, and reflected through the longitudinal axis 71, such that rib side surface points 59 may also be intersection surfaces of two planar longitudinal surfaces, each of which may be co-planar to a plane that is at an acute angle relative to the plane that perpendicularly cross-sects the proximal-distal longitudinal axis 71. Such rotation-reflection symmetry may be without respect to the positions of any tab mounts or tab mount holes, or bottom rib opening 51, which may not be included in the rotation-reflection symmetry.

Figure 9A:
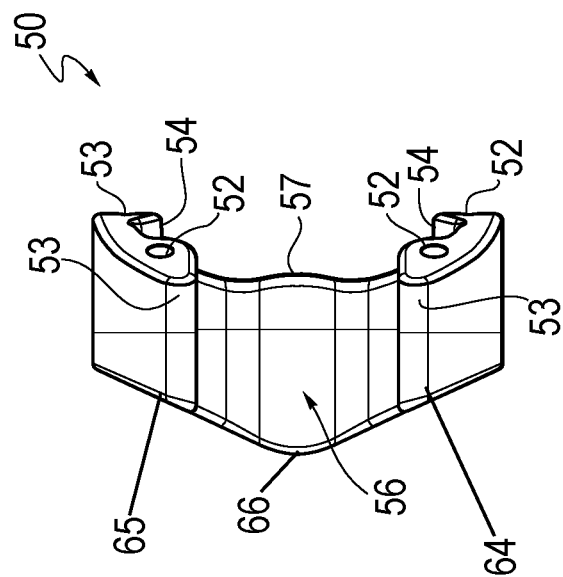
FIGS. 9A and 9B illustrate a view of the symmetry associated with an example of a circumferentially continuous, C-shaped, or open rib for an example of an endoscope system constructed according to the principles of the present disclosure.
Figure 9B:
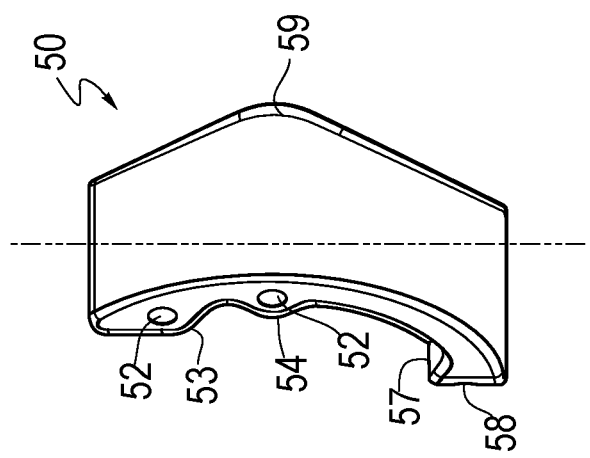

FIGS. 9A and 9B illustrate a view of the rotation-reflection symmetry associated with an example of a circumferentially uncontinuous rib 50 for an example of an endoscope system 10 constructed according to the principles of the present disclosure. FIG. 9A illustrates a side view of a circumferentially uncontinuous rib 50. As FIG. 9A demonstrates, rib side surface point 59 may be an intersection surface of two planar longitudinal surfaces. FIG. 9B illustrates a top view of a circumferentially uncontinuous rib 50, which corresponds to a 90-degree rotation-reflection about the longitudinal axis 71 of the circumferentially uncontinuous rib 50 illustrated in FIG. 9A. As FIG. 9B demonstrates, planar side longitudinal surfaces 64, 65 may intersect at intersection surfaces 66 similarly to two planar longitudinal surfaces intersecting at rib side surface point 59 in FIG. 9A. The 90-degree rotation-reflection symmetry of ring-shaped ribs 40 and circumferentially uncontinuous ribs 50 advantageously provide for four-way deflection of the bending section of the distal portion 12 of the endoscope system 10. The bending section may advantageously move exactly laterally, rather than at an angle. Further, such 90-degree rotation-reflection symmetry advantageously provides for bending of the bending section equally left (i.e., "a first direction") and right (i.e., "a second direction," opposite to the first direction) in the horizontal plane including longitudinal axis 71 and up (i.e., "a third direction," perpendicular to the first direction and perpendicular to the second direction) and down (i.e., "a fourth direction," opposite to the third direction) in the vertical plane 70.

FIGS. 10 and 11 illustrate detailed views of an example of a distal portion 12 of an endoscope system 10 constructed in accordance with the principles of the present disclosure. FIG. 10 illustrates a top view of an example of a distal portion 12 of an endoscope system 10 constructed in accordance with the principles of the present disclosure. The distal portion 12 of endoscope system 10 may include one or more ring-shaped ribs 40 at the proximal end of the distal portion 12. The one or more ring-shaped ribs 40 are arranged sequentially in opposite orientations, with the proximal-most ring-shaped rib 40 arranged such that intersection surface 63 may be directed distally. The adjacent ring-shaped rib 40 to the proximal-most ring-shaped rib 40 is arranged such that the intersection surface 63 may be directed proximally to confront the intersection surface 63 of the proximal-most ring-shaped rib 40. The next distal ring-shaped rib 40 in sequence is arranged such that the intersection surface 63 may be directed distally. The bending section may include further distal ring-shaped ribs 40 in pairs, and such pairs may be arranged such that the intersection surface 63 of the distal-most ring-shaped rib 40 may be directed distally. Planar side longitudinal surface 61 of the proximal-most ring-shaped rib 40 and planar side longitudinal surface 62 of the adjacent ring-shaped rib 40 to the proximal-most ring-shaped rib 40 may form an angle. Depending upon left and right movement of the bending section during operation, the angle between a planar side longitudinal surface 61 directed proximally and a planar side longitudinal surface 62 of an adjacent ring-shaped rib 40 directed distally may be an angle from about 5 degrees to about 90 degrees, preferably from about 40 degrees to about 60 degrees.

The bending section will include one or more circumferentially uncontinuous ribs 50 distal to the distal-most ring-shaped rib 40. The proximal-most circumferentially uncontinuous rib 50 may be arranged such that intersection surface 66 may be directed proximally to confront the intersection surface 63 of the distal-most ring-shaped rib 40. Planar side longitudinal surface 61 of the distal-most ring-shaped rib 40 and planar side longitudinal surface 64 of the proximal-most circumferentially uncontinuous rib 50 may form an angle denoted in FIG. 10 by α. Depending upon left and right movement of the bending section during operation, the angle α may be an angle from about 5 degrees to about 90 degrees, preferably from about 40 degrees to about 60 degrees. The bending section may include further circumferentially uncontinuous ribs 50 in pairs, and such pairs may be arranged such that the intersection surface 66 of the distal-most circumferentially uncontinuous rib 50 may be directed proximally. Planar side longitudinal surface 64 of a circumferentially uncontinuous rib 50 directed distally and planar side longitudinal surface 65 of an adjacent circumferentially uncontinuous rib 50 directed proximally may form an angle. Depending upon left and right movement of the bending section during operation, the angle between planar side longitudinal surface 64 and adjacent planar side longitudinal surface 65 may be an angle from about 5 degrees to about 90 degrees, preferably from about 40 degrees to about 60 degrees.

FIG. 11 illustrates a side view of an example of a distal portion 12 of an endoscope system 10 constructed in accordance with the principles of the present disclosure. While the proximal-most ring-shaped rib 40 is arranged such that the intersection surface 63 may be directed distally, due to the advantageous 90-degree rotation-reflection symmetry of ring-shaped rib 40, the rib side surface point 49 may be directed proximally, as illustrated by FIG. 11. The two ring-shaped ribs 40 adjacent to the proximal-most ring-shaped rib 40 are arranged such that the rib side surface point 49 of one ring-shaped rib 40 confronts the rib side surface point 49 of the adjacent ring-shaped rib 40, as illustrated by FIG. 11. Planar side longitudinal surfaces of ring-shaped ribs 40 intersect at rib side surface point 49 such that adjacent ring-shaped ribs 40 that confront each other at their rib side surface points 49 may form an angle between planar side longitudinal surfaces of adjacent ring-shaped ribs 40. Depending upon up and down movement of the bending section during operation, the angle between planar side longitudinal surfaces may be an angle from about 5 degrees to about 90 degrees, preferably from about 40 degrees to about 60 degrees. Planar side longitudinal surfaces of circumferentially uncontinuous ribs 50 intersect at rib side surface points 59 such that adjacent circumferentially uncontinuous ribs 50 that confront at their rib side surface points 59 may form an angle between planar side longitudinal surfaces of adjacent circumferentially uncontinuous ribs 50. Depending upon up and down movement of the bending section during operation, the angle between planar side longitudinal surfaces may be an angle from about 5 degrees to about 90 degrees, preferably from about 40 degrees to about 60 degrees.

Figure 16:
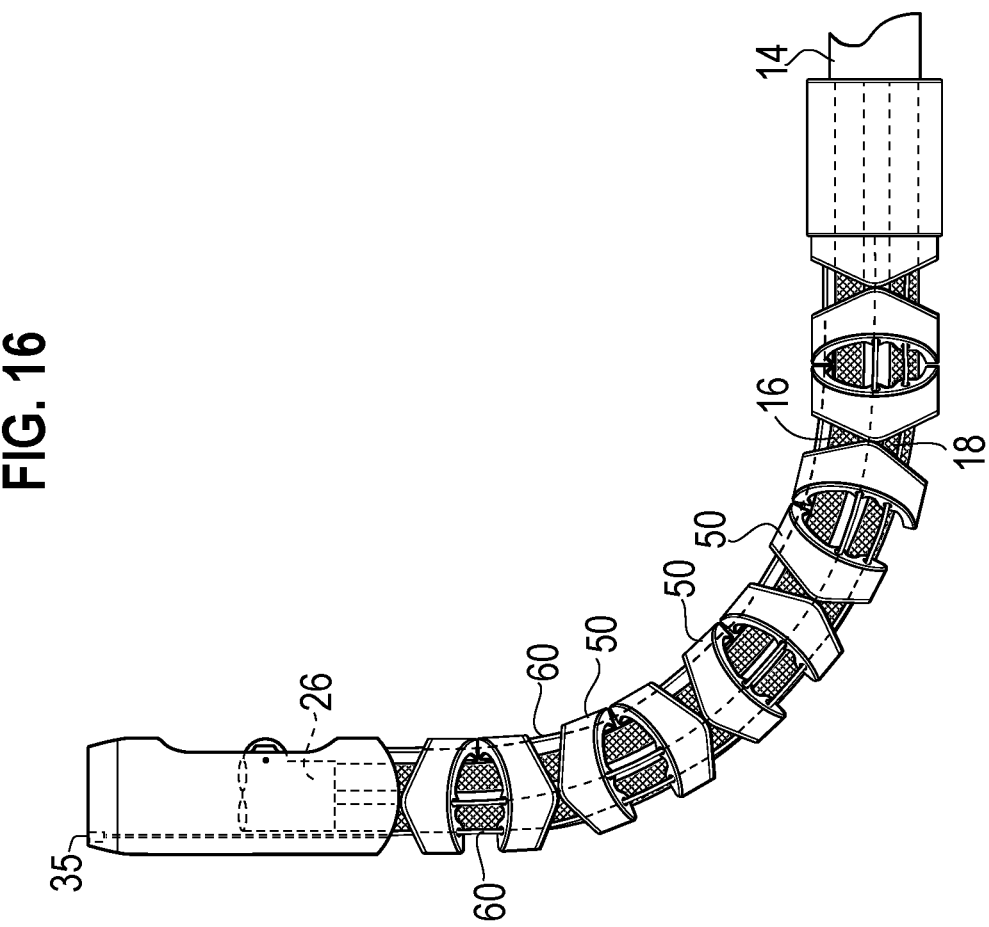
FIG. 16 illustrates a detailed view of a distal portion of an example of an endoscope system in a bent configuration.

FIG. 12 illustrates another example of an assembly of an example of ribs 22 of on a series of one or more control wires 60. Control wires 60 may be fixedly attached to the distal end section 24 and extend in parallel through, or outside of the at least one lumen 15 to handle portion 13. Alternatively, the control wires 60 may extend through dedicated low friction lumens or catheters along the length of the endoscope system 10 to the handle portion 13. A first control wire 60 may be fixed on a wall of the distal end section 24 such that control wire 60 passes through top tab mount lumen 58 of one or more circumferentially uncontinuous ribs 50 and through top tab mount lumen 48 of one or more ring-shaped ribs 40. Additional control wires 60 may be fixed in advantageous positions on the wall of the distal end section 24 such that a control wire 60 passes through a side tab mount lumen 52 of the one or more circumferentially uncontinuous ribs 50 and through a corresponding side tab mount lumen 42 of the one or more ring-shaped ribs 40, as illustrated in FIG. 12. An endoscope system 10 may include three, four, five, or more control wires 60. In addition to the ability to switch between forward-viewing and side-viewing configurations, the distal portion 12 of the endoscope system 10 may also bend and rotate as desired advantageously. FIG. 15 illustrates the distal portion 12 in a straight configuration such that the control wires 60 are straight and parallel, while FIG. 16 illustrates the distal portion 12 in a bent configuration, such that the control wires 60 are parallel but not straight. To move the distal portion 12 from the straight configuration illustrated in FIG. 15 to the bent configuration illustrated in FIG. 16, a control wire 60 may be pulled in a proximal direction. The proximal movement of the control wire 60 may result in a force being applied through the control wire 60 and to the distal end section 24. This force may cause the flexible, ribbed body of the distal portion 12 to bend as illustrated in FIG. 15. To move the distal portion 12 back to the straight configuration, second and third control wires 60 opposite to the initially-pulled control wire 60 may be pulled in a proximal direction. Because the second and third control wires 60 are connected to the opposite side of the distal end section 24, a force is applied through the second and third control wires 60 and to the distal end section 24 that may move the distal portion 12 back towards the straight configuration. The side tab mount lumens 42 and 52 of the ring-shaped rib 40 and circumferentially uncontinuous rib 50, respectfully, may be advantageously arranged such that control wires 60 may allow for force to be applied through the control wires 60 and to the distal end section 24, and reversibly move the distal end section 24 up, down, left, or right. The side tab mount lumens 42 and 52 may be advantageously positioned on the one or more ring-shaped ribs 40 and the one or more circumferentially uncontinuous ribs 50 such that the bending section will not be pulled off-plane, which allows for the bending section to move advantageously exactly laterally rather than at an angle and which force transmission is not increased by pulling a ring-shaped rib 40 or circumferentially uncontinuous rib 50 at a moment. Circumferentially uncontinuous ribs 50 may be arranged on control wires 60 such that the bottom rib openings 51 may be aligned longitudinally, such that the bottom rib openings 51 are open to the same direction, or coaxial.

Figure 17:
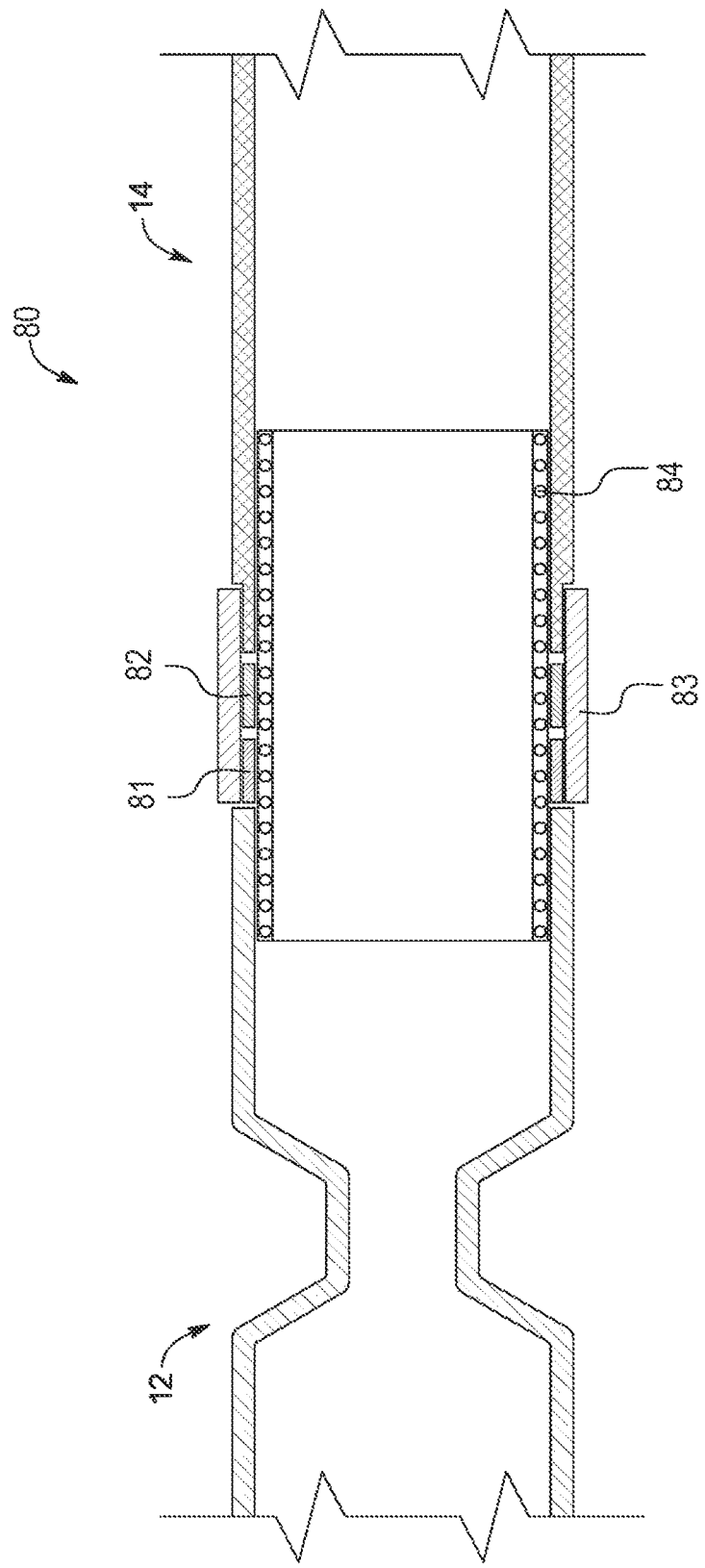
FIG. 17 illustrates a detailed view of an example of an axially rotatable bearing of an example of an endoscope system.

FIG. 17 illustrates a detailed view of an example of an axially rotatable bearing 80 of an example of an endoscope system 10 and its functionality. The axially rotatable bearing 80 may include a first ring 81 and a second ring 82. The axially rotatable bearing 80 may further include a first tube 83 and a second tube 84. The first tube 83 may be fixedly attached to the central portion 14 and the first ring 81. The second tube 84 may be fixedly attached to the distal portion 12 and the second ring 82. The first tube 83 and first ring 81 may be freely rotatable with respect to the second tube 84 and second ring 82, thereby making the distal portion 12 freely rotatable with respect to the central portion 14. Because the first ring 81 is indirectly secured to the central portion 14, but is located distal to the second ring 82, which is indirectly secured to the distal portion 12, the distal portion 12 and central portion 14 may remain secured to each other while still remaining freely rotatable with respect to each other. The distal portion 12 may be freely rotated when the endoscope system 10 is in any one of the configurations described above, including forward-viewing configuration, side-viewing configuration, straight configuration, and bent configuration. The accessory channels 16, 18 and the control wires 60 may pass freely through lumen 15 of the axially rotatable bearing 80 while causing no or minimal interference to the axially rotatable bearing 80. This is merely one potential design for the axially rotatable bearing 80, and various other designs that allow free rotation of the distal portion 12 with respect to the central portion 14 may be used.

Control wires 60 may also advantageously secure the one or more ring-shaped ribs 40 and the one or more circumferentially uncontinuous ribs 50 of the distal portion 12 together. Sufficient tension may be applied to the control wires 60, thereby advantageously securing together the one or more ring-shaped ribs 40 and the one or more circumferentially uncontinuous ribs 50 along the control wires 60. Due to this design, the one or more ring-shaped ribs 40 and the one or more circumferentially uncontinuous ribs 50 may be advantageously shaped to allow for minimal contact between the individual one or more ring-shaped ribs 40 and/or the one or more circumferentially uncontinuous ribs 50. Optionally, one or more control wires 60 may include built-in electrical wiring from an electrical power source that allows the one or more control wires 60 to function as a circuit for the LED light 35 as well. Alternatively, or in addition to the one or more control wires 60, the one or more ring-shaped ribs 40 and/or the one or more circumferentially uncontinuous ribs 50 may be connected together using a variety of other methods, such as with mechanical hinges, adhesives, and other well-known devices. Further, additional elongate members may extend through the top tab mount lumens 48 and 58 and/or side tab mount lumens 42 and 52 similarly to the one or more control wires 60 to provide additional support to the distal portion 12.

Additionally, the one or more ring-shaped ribs 40 and the one or more circumferentially uncontinuous ribs 50 may be covered by a protective sleeve that may be made up of various biocompatible materials, such as an elastomeric material. The protective sleeve may protect the one or more ring-shaped ribs 40 and the one or more circumferentially uncontinuous ribs 50 while also preventing body tissue from accidentally being pinched between the individual one or more ring-shaped ribs 40 and the one or more circumferentially uncontinuous ribs 50 when the distal portion 12 is moved between the bent configuration and the straight configuration. The protective sleeve may also include a slot that corresponds to the bottom rib openings 51 in the circumferentially uncontinuous ribs 50 that allows the accessory channels 16, 18 to move outside of the protective sleeve and between the forward-viewing configuration and the side-viewing configuration. The protective sleeve may also advantageously assist torque transmission when moving the distal portion 12 between the bent configuration and the straight configuration. Some natural lag may occur when manipulating the one or more control wires 60 that may cause part of the distal portion 12 to move initially, while the remainder of the distal portion 12 lags behind, but eventually moves as well. The protective sleeve may advantageously ensure that the entire distal portion 12 moves together and with minimal lag.

The endoscope system 10 may move between a bent configuration and a straight configuration while the endoscope system 10 may also be in either the forward-viewing or side-viewing configurations. For example, FIG. 15 illustrates that the endoscope system 10 in a straight and side-viewing configuration. The endoscope system 10 may be manipulated and used in any combination of the above-mentioned configurations, and may be repeatedly movable between all configurations.

The accessory channels 16, 18 may be used to provide access for a variety of medical tools and accessories through the endoscope system 10 and into a patient's body. For example, a camera system may be inserted into one of the accessory channels 16, while a variety of tools including, but not limited to, forceps, sphincterotomes, wires, dilation balloons, extraction balloons, stents, needle knives, hemostasis clips, and any other catheter-based tool may be inserted into the other accessory channel 18. The tools may be advanced past the distal ends of the accessory channels 16, 18 where they may be used to operate on a patient.

The endoscope system 10, or any portion thereof, may be designed to be disposable, thus reducing the risk of bacterial infection due to incomplete cleaning between uses.

The present disclosure further contemplates methods of using an endoscope system 10, including the steps of: inserting the endoscope system 10 into a patient's body, the endoscope system 10 including an elongate tube including at least one lumen 15 and one or more accessory channels 16, 18 movably disposed at least partially within the at least one lumen 15 of the elongate tube, the one or more accessory channels 16, 18 including a tubular structure including first and second accessory lumens 28, 30 extending therethrough; and moving a control wire 60 so as to bend the distal portion 12 of the elongate tube in a first direction.

A method of using an endoscope system 10 may further include the step of: positioning the endoscope system 10 in a forward-viewing configuration, wherein in the forward-viewing configuration the distal end section 24 of the one or more accessory channels 16, 18 is substantially parallel to the distal portion 12 of the elongate tube.

A method of using an endoscope system 10 may further include the step of: moving the endoscope system 10 to a side-viewing configuration wherein in the side-viewing configuration, the distal end section 24 of the one or more accessory channels 16, 18 is arced at a radius greater than a radius of the distal portion 12 of the elongate tube. The step of moving the endoscope system 10 to a side-viewing configuration may further include rotating the distal end section 24 of the one or more accessory channels 16, 18 about a pivot point of the distal portion 12 of the elongate tube.

A method of using an endoscope system 10 may further include the step of: moving a second control wire 60 so as to bend the distal portion 12 of the elongate tube in a second direction, the second direction opposite to the first direction.

A method of using an endoscope system 10 may further include the step of: moving a third control wire 60 so as to bend the distal portion 12 of the elongate tube in a third direction, the third direction perpendicular to the first direction and perpendicular to the second direction.

A method of using an endoscope system 10 may further include the step of: moving a fourth control wire 60 so as to bend the distal portion 12 of the elongate tube in a fourth direction, the fourth direction opposite to the third direction.

A method of using an endoscope system 10 may further include the step of: moving the endoscope system 10 from the side-viewing configuration back to the forward-viewing configuration.

A method of using an endoscope system 10 may further include the step of: removing the one or more accessory channels 16, 18 from the interior cavity 56 of the one or more circumferentially uncontinuous ribs 50.

Although the present disclosure has been described with reference to examples and the accompanying drawings, the present disclosure is not limited thereto, but may be variously modified and altered by those skilled in the art to which the present disclosure pertains without departing from the spirit and scope of the present disclosure.

The subject-matter of the present disclosure may also relate, among others, to the following aspects:

A first aspect relates to a scope system, the scope system comprising: an elongate tube comprising a lumen extending therethrough, the elongate tube further comprising a distal portion; at least one accessory channel comprising a tubular structure comprising an accessory lumen extending therethrough, the at least one accessory channel movably disposed at least partially within the lumen, the at least one accessory channel comprising a distal end section; a first control wire, connected to the distal portion of the elongate tube and extending proximally along the elongate tube; a second control wire, connected to the distal portion of the elongate tube and extending proximally along the elongate tube, parallel to the first control wire; a third control wire, connected to the distal portion of the elongate tube and extending proximally along the elongate tube, parallel to the first control wire and the second control wire; and a fourth control wire, connected to the distal portion of the elongate tube and extending proximally along the elongate tube, parallel to the first control wire, the second control wire, and the third control wire; wherein proximal movement of the first control wire bends the distal portion in a first direction; wherein proximal movement of the second control wire bends the distal portion in a second direction, the second direction opposite to the first direction; wherein proximal movement of the third control wire bends the distal portion in a third direction, the third direction perpendicular to the first direction and perpendicular to the second direction; and wherein proximal movement of the fourth control wire bends the distal portion in a fourth direction, the fourth direction opposite to the third direction.

A second aspect relates to the scope system of aspect 1, wherein the distal portion comprises a plurality of circumferentially uncontinuous ribs, each of the plurality of circumferentially uncontinuous ribs comprising a rib opening, the rib openings of the plurality of circumferentially uncontinuous ribs being coaxial; wherein each of the plurality of circumferentially uncontinuous ribs surrounds the at least one accessory channel; and wherein the at least one accessory channel is reversibly removable from an interior cavity of each of the plurality of circumferentially uncontinuous ribs through the rib openings.

A third aspect relates to the scope system of any preceding aspect, wherein the distal portion further comprises: a plurality of ring-shaped ribs, each of the plurality of ring-shaped ribs generally 90-degree rotation-reflection symmetrical about a proximal-distal longitudinal axis, each of the plurality of ring-shaped ribs encircling the at least one accessory channel, each of the plurality of ring-shaped ribs comprising a ring-shaped rib proximal surface and a ring-shaped rib distal surface, the ring-shaped rib proximal surface comprising a plurality of ring-shaped rib planar surfaces and the ring-shaped rib distal surface comprising a plurality of ring-shaped rib planar surfaces, each of the plurality of ring-shaped rib planar surfaces at an angle of less than 90 degrees relative to a cross-sectional plane, the cross-sectional plane cross-secting the proximal-distal longitudinal axis; each of the plurality of circumferentially uncontinuous ribs generally 90-degree rotation-reflection symmetrical about the proximal-distal longitudinal axis, each of the plurality of circumferentially uncontinuous ribs further comprising a proximal surface and a distal surface, the proximal surface comprising a plurality of planar faces and the distal surface comprising a plurality of planar surfaces, each of the plurality of planar surfaces at an angle of less than 90 degrees relative to the cross-sectional plane; and wherein the first control wire, the second control wire, the third control wire, and the fourth control wire connect the plurality of ring-shaped ribs and the plurality of circumferentially uncontinuous ribs.

A fourth aspect relates to the scope system of any preceding aspect, wherein the at least one accessory channel is movable between a forward-viewing configuration and a side-viewing configuration; wherein in the forward-viewing configuration, the distal end section is substantially parallel to the distal portion; and wherein in the side-viewing configuration, the distal end section is disposed at an angle of curvature relative to the distal portion.

A fifth aspect relates to the scope system of any preceding aspect, wherein the distal end section is rotatably coupled to the distal portion.

A sixth aspect relates to the scope system of any preceding aspect, further comprising an axially rotatable bearing disposed between the distal portion and a proximal portion of the elongate tube, the axially rotatable bearing permitting rotation of the distal portion about a proximal-distal longitudinal axis relative to the proximal portion.

A seventh aspect relates to the scope system of any preceding aspect, further comprising a light connected to the distal portion, wherein one of the first control wire, the second control wire, the third control wire, and the fourth control wire further comprises an electrical wiring between the light and a power source.

An eighth aspect relates to the scope system of any preceding aspect, wherein a camera system is at least partially and removably disposed within the at least one accessory lumen.

A ninth aspect relates to the scope system of any preceding aspect, wherein the at least one accessory lumen is configured to receive a tool.

A tenth aspect relates to the scope system of any preceding aspect, wherein the plurality of circumferentially uncontinuous ribs is distal to the plurality of ring-shaped ribs.

An eleventh aspect relates to the scope system of any preceding aspect, wherein the angle between a planar surface of a circumferentially uncontinuous rib and a second planar surface of an adjacent circumferentially uncontinuous rib that faces the planar surface is from about 5 degrees to about 90 degrees.

A twelfth aspect relates to the scope system of any of aspects 2 to 11, wherein the angle between a planar surface of a circumferentially uncontinuous rib and a third planar surface of an adjacent ring-shaped rib that faces the planar surface is from about 5 degrees to about 90 degrees.

A thirteenth aspect relates to the scope system of any of aspects 2 to 11, wherein the angle between a fourth planar surface of a ring-shaped rib and a fifth planar surface of an adjacent ring-shaped rib that faces the fourth planar surface is from about 5 degrees to about 90 degrees.

A fourteenth aspect relates to the scope system of any of aspects 2 to 13, further comprising a fifth control wire; wherein proximal movement of the fourth control wire and the fifth control wire bend the distal portion in the fourth direction; and wherein the fifth control wire connects the plurality of ring-shaped ribs and the plurality of circumferentially uncontinuous ribs.

A fifteenth aspect relates to the scope system of any of aspects 4 to 14, wherein in the side-viewing configuration, the angle of curvature is greater than an angle of distal portion curvature.

A sixteenth aspect relates to the scope system of any of aspects 4 to 14, wherein in the forward-viewing configuration, the distal end section is substantially disposed within the lumen of the distal portion.

A seventeenth aspect relates to the scope system of any of aspects 4 to 14, wherein movement of a proximal portion of the at least one accessory channel in a distal direction relative to the elongate tube moves the at least one accessory channel from the forward-viewing configuration to the side-viewing configuration.

An eighteenth aspect relates to the scope system of any of aspects 4 to 14, wherein movement of a proximal portion of the at least one accessory channel in a proximal direction relative to the elongate tube moves the at least one accessory channel from the side-viewing configuration to the forward-viewing configuration.

A nineteenth aspect relates to a method of using a scope system, comprising: inserting an endoscope system into a patient's body, the endoscope system comprising: an elongate tube comprising a lumen therethrough, the elongate tube further comprising a distal portion; at least one accessory channel comprising a tubular structure comprising an accessory lumen extending therethrough, the at least one accessory channel movably disposed at least partially within the lumen, the at least one accessory channel comprising a distal end section; and a plurality of parallel control wires, each of the plurality of parallel control wires connected to the distal portion of the elongate tube and extending proximally along the elongate tube, individual proximal movement of one or more of the plurality of parallel control wires bending the distal portion in one of a first direction, a second direction, a third direction, and a fourth direction, the second direction opposite the first direction, the third direction perpendicular to the first direction and perpendicular to the second direction, and the fourth direction opposite the third direction; moving one or more of the plurality of parallel control wires so as to bend the distal portion in one of the first direction, the second direction, the third direction, and the fourth direction; positioning the endoscope system in a forward-viewing configuration, wherein in the forward-viewing configuration the distal end section is substantially parallel to the distal portion; and moving the endoscope system to a side-viewing configuration wherein in the side-viewing configuration, the distal end section is disposed at an angle of curvature greater than an an angle of distal portion curvature.

In addition to the features mentioned in each of the independent aspects enumerated above, some examples may show, alone or in combination, the optional features mentioned in the dependent aspects and/or as disclosed in the description above and shown in the figures.

What is claimed is:

1. A scope system, comprising:
    an elongate tube comprising a lumen extending therethrough, the elongate tube further comprising a distal portion, the distal portion comprising a plurality of ring-shaped ribs and a plurality of circumferentially uncontinuous ribs, each of the plurality of circumferentially uncontinuous ribs comprising a rib opening;
    at least one accessory channel comprising a tubular structure comprising an accessory lumen extending therethrough, the at least one accessory channel movably disposed at least partially within the lumen, the at least one accessory channel comprising a distal end section, each of the plurality of ring-shaped ribs encircling the at least one accessory channel and each of the plurality of circumferentially uncontinuous ribs partially encircling the at least one accessory channel;
    a first control wire, connected to the distal portion of the elongate tube and extending proximally along the elongate tube;
    a second control wire, connected to the distal portion of the elongate tube and extending proximally along the elongate tube;

a third control wire, connected to the distal portion of the elongate tube and extending proximally along the elongate tube; and a fourth control wire, connected to the distal portion of the elongate tube and extending proximally along the elongate tube;

wherein proximal movement of the first control wire bends the distal portion in a first direction;

wherein proximal movement of the second control wire bends the distal portion in a second direction opposite to the first direction;

wherein proximal movement of the third control wire bends the distal portion in a third direction, the third direction perpendicular to the first direction and perpendicular to the second direction;

wherein proximal movement of the fourth control wire bends the distal portion in a fourth direction opposite to the third direction;

wherein the first control wire, the second control wire, the third control wire, and the fourth control wire connect the plurality of ring-shaped ribs and the plurality of circumferentially uncontinuous ribs;

wherein the rib openings of the plurality of circumferentially uncontinuous ribs are coaxial; and wherein the at least one accessory channel is reversibly movable laterally from an interior cavity of each of the plurality of circumferentially uncontinuous ribs through the rib openings.

2. The scope system of claim 1, wherein each of the plurality of ring-shaped ribs comprises a ring-shaped rib proximal surface and a ring-shaped rib distal surface, the ring-shaped rib proximal surface comprising a plurality of ring-shaped rib planar surfaces and the ring-shaped rib distal surface comprising a plurality of ring-shaped rib planar surfaces, each of the plurality of ring-shaped rib planar surfaces at an angle of less than 90 degrees relative to a cross-sectional plane, the cross-sectional plane cross-setting a proximal-distal longitudinal axis; and wherein each of the plurality of circumferentially uncontinuous ribs comprises a proximal surface and a distal surface, the proximal surface comprising a plurality of planar surfaces and the distal surface comprising a plurality of planar surfaces, each of the plurality of planar surfaces at an angle of less than 90 degrees relative to the cross-sectional plane.

3. The scope system of claim 2, wherein the plurality of circumferentially uncontinuous ribs is distal to the plurality of ring-shaped ribs.

4. The scope system of claim 2, wherein the angle between a planar surface of a circumferentially uncontinuous rib and a second planar surface of an adjacent circumferentially uncontinuous rib that faces the planar surface is from about 5 degrees to about 90 degrees.

5. The scope system of claim 2, wherein the angle between a planar surface of a circumferentially uncontinuous rib and a third planar surface of an adjacent ring-shaped rib that faces the planar surface is from about 5 degrees to about 90 degrees.

6. The scope system of claim 2, wherein the angle between a fourth planar surface of a ring-shaped rib and a fifth planar surface of an adjacent ring-shaped rib that faces the fourth planar surface is from about 5 degrees to about 90 degrees.

7. The scope system of claim 2, further comprising a fifth control wire;

wherein proximal movement of the fourth control wire and the fifth control wire bend the distal portion in the fourth direction; and wherein the fifth control wire connects the plurality of ring-shaped ribs and the plurality of circumferentially uncontinuous ribs.

8. The scope system of claim 1, wherein the at least one accessory channel is movable between a forward-viewing configuration and a side-viewing configuration;

wherein in the forward-viewing configuration, the distal end section is substantially parallel to the distal portion; and wherein in the side-viewing configuration, the distal end section is disposed at an angle of curvature relative to the distal portion.

9. The scope system of claim 8, wherein in the side-viewing configuration, the angle of curvature is greater than an angle of distal portion curvature.

10. The scope system of claim 8, wherein in the forward-viewing configuration, the distal end section is substantially disposed within the lumen of the distal portion.

11. The scope system of claim 8, wherein movement of a proximal portion of the at least one accessory channel in a distal direction relative to the elongate tube moves the at least one accessory channel from the forward-viewing configuration to the side-viewing configuration.

12. The scope system of claim 8, wherein movement of a proximal portion of the at least one accessory channel in a proximal direction relative to the elongate tube moves the at least one accessory channel from the forward-viewing configuration to the side-viewing configuration.

13. The scope system of claim 1, wherein the distal end section is rotatably coupled to the distal portion.

14. The scope system of claim 1, further comprising an axially rotatable bearing disposed between the distal portion and a proximal portion of the elongate tube, the axially rotatable bearing permitting rotation of the distal portion about a proximal-distal longitudinal axis relative to the proximal portion.

15. The scope system of claim 1, further comprising a light connected to the distal portion, wherein one of the first control wire, the second control wire, the third control wire, and the fourth control wire further comprises an electrical wiring between the light and a power source.

16. The scope system of claim 1, wherein a camera system is at least partially and removably disposed within the at least one accessory lumen.

17. The scope system of claim 1, wherein the at least one accessory lumen is configured to receive a tool.

18. The scope system of claim 1, wherein the first control wire, the second control wire, the third control wire, and the fourth control wire are parallel.

19. A scope system, comprising:
an elongate tube comprising a lumen extending therethrough, the elongate tube further comprising a distal portion, the distal portion comprising a plurality of ring-shaped ribs and a plurality of circumferentially uncontinuous ribs, each of the plurality of circumferentially uncontinuous ribs comprising a rib opening, the rib openings of the plurality of circumferentially uncontinuous ribs being coaxial;

at least one accessory channel comprising a tubular structure comprising an accessory lumen extending therethrough, each of the plurality of ring-shaped ribs encircling the at least one accessory channel and each of the plurality of circumferentially uncontinuous ribs partially encircling the at least one accessory channel, the at least one accessory channel movably disposed at least partially within the lumen, the at least one accessory channel comprising a distal end section;

a first control wire, connected to the distal portion of the elongate tube and extending proximally along the elongate tube;

a second control wire, connected to the distal portion of the elongate tube and extending proximally along the elongate tube;

a third control wire, connected to the distal portion of the elongate tube and extending proximally along the elongate tube; and a fourth control wire, connected to the distal portion of the elongate tube and extending proximally along the elongate tube;

wherein proximal movement of the first control wire bends the distal portion in a first direction;

wherein proximal movement of the second control wire bends the distal portion in a second direction;

wherein proximal movement of the third control wire bends the distal portion in a third direction;

wherein proximal movement of the fourth control wire bends the distal portion in a fourth direction; and wherein the at least one accessory channel is reversibly movable laterally from an interior cavity of each of the plurality of circumferentially uncontinuous ribs through the rib openings.

20. The scope system of claim 19, wherein the at least one accessory channel is movable between a forward viewing configuration and a side-viewing configuration;

wherein in the forward-viewing configuration, the distal end section is substantially parallel to the distal portion; and wherein in the side-viewing configuration, the distal end section is disposed at an angle of curvature greater than an angle of distal portion curvature.

21. The scope system of claim 19, wherein the first control wire, the second control wire, the third control wire, and the fourth control wire are parallel.

* * * * *

UNITED STATES PATENT AND TRADEMARK OFFICE
CERTIFICATE OF CORRECTION

| | |
|---|---|
| PATENT NO. | : 11,839,359 B2 |
| APPLICATION NO. | : 17/341842 |
| DATED | : December 12, 2023 |
| INVENTOR(S) | : John Crowder Sigmon, Jr. et al. |

It is certified that error appears in the above-identified patent and that said Letters Patent is hereby corrected as shown below:

In the Claims

Column 19, Claim 2, Line 37, delete "cross-setting" and replace with --cross-secting--

Signed and Sealed this
Twenty-seventh Day of February, 2024

Katherine Kelly Vidal
*Director of the United States Patent and Trademark Office*